United States Patent [19]

Andert et al.

[11] Patent Number: 4,821,320

[45] Date of Patent: Apr. 11, 1989

[54] DEVICE FOR PROTECTING ELECTRICAL APPARATUS AND THE OPERATOR WHEN THE OPERATOR CARRIES A HIGH ELECTROSTATIC CHARGE

[75] Inventors: Tomas J. Andert, Bocholt; Stefan Pieper, Haltern, both of Fed. Rep. of Germany

[73] Assignee: Siemens Aktiengesellschaft, Berlin and Munich, Fed. Rep. of Germany

[21] Appl. No.: 53,996

[22] Filed: May 26, 1987

[30] Foreign Application Priority Data

May 27, 1986 [DE] Fed. Rep. of Germany ....... 3617734

[51] Int. Cl.[4] .............................................. H04M 1/03
[52] U.S. Cl. .................................... 379/437; 379/433; 361/212
[58] Field of Search ............... 379/370, 387, 412, 451, 379/428, 437, 433; 361/212, 200

[56] References Cited

U.S. PATENT DOCUMENTS

| | | | |
|---|---|---|---|
| 3,627,930 | 12/1971 | Tolman | 379/370 |
| 3,653,498 | 4/1972 | Kisor | 361/212 X |
| 3,711,742 | 1/1973 | Pinkham, Jr. | 361/220 X |
| 4,040,120 | 8/1977 | Geadah et al. | 379/428 X |
| 4,124,785 | 11/1978 | Seretny et al. | 379/370 |
| 4,192,976 | 3/1980 | Scott | 379/368 X |
| 4,271,333 | 6/1981 | Adams et al. | 379/368 |
| 4,303,960 | 12/1981 | Sherwood et al. | 361/220 X |
| 4,440,990 | 4/1984 | Nozaki | 200/5 |
| 4,456,800 | 6/1984 | Holland | 361/220 X |
| 4,586,106 | 4/1986 | Frazier | 361/220 X |
| 4,654,628 | 3/1987 | Takayanagi | 361/220 X |
| 4,667,266 | 5/1987 | Masuoka et al. | 361/212 |

Primary Examiner—Eugene R. Laroche
Assistant Examiner—Seung Ham
Attorney, Agent, or Firm—Lawrence C. Edelman

[57] ABSTRACT

A device for protecting both the operator of an electronic apparatus and the electronic equipment of the apparatus when the operator carries a high electrostatic charge. To ensure a gentle electrostatic discharge of the operator, resistance paths which lead to an ground point of the electronic apparatus are arranged in the danger zone of the apparatus.

6 Claims, 4 Drawing Sheets

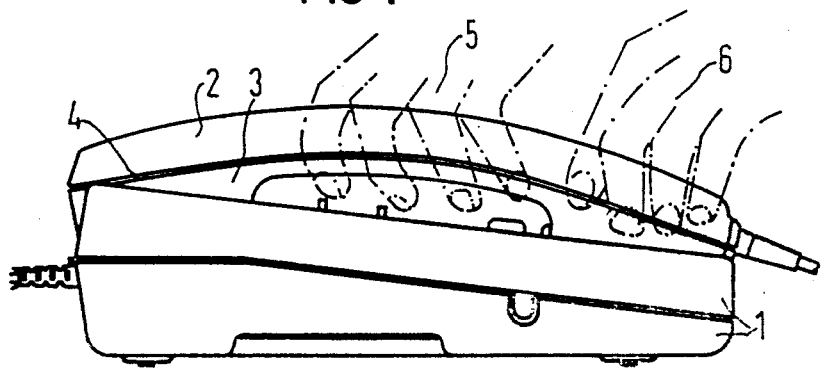
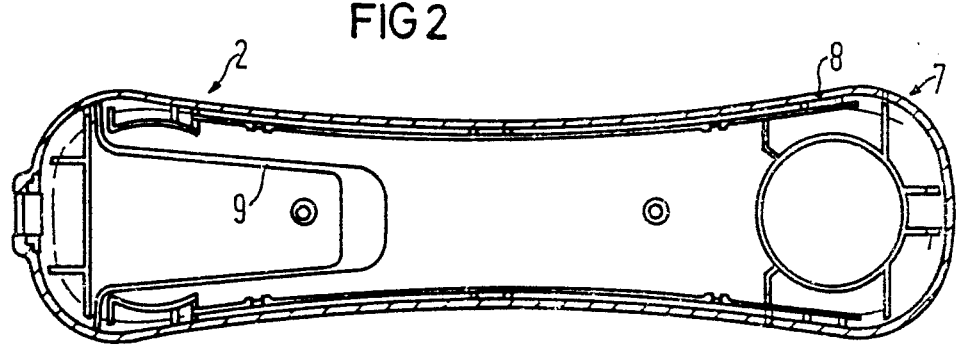
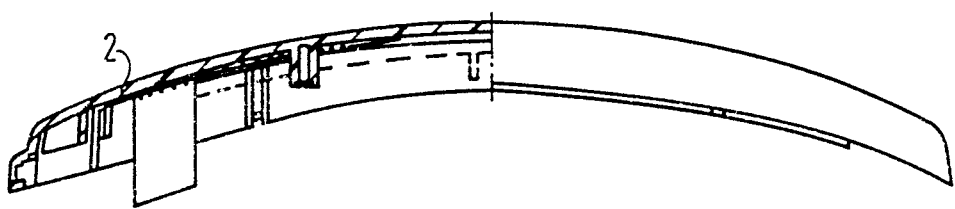

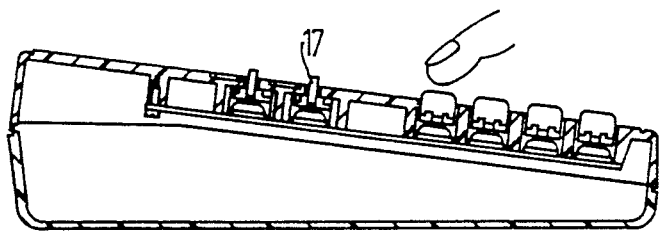
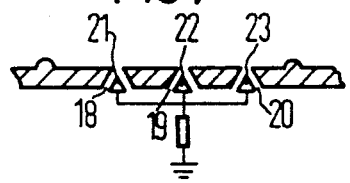
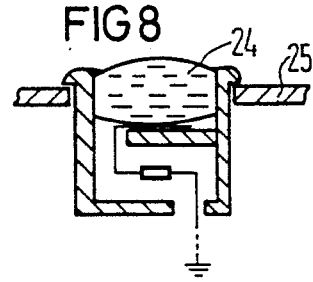
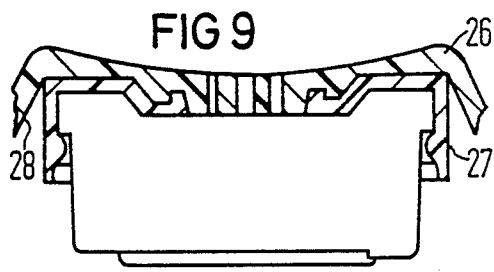
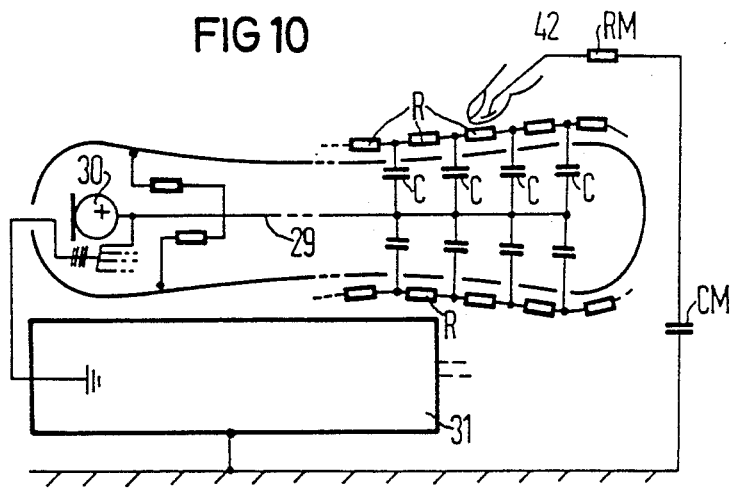

DEVICE FOR PROTECTING ELECTRICAL APPARATUS AND THE OPERATOR WHEN THE OPERATOR CARRIES A HIGH ELECTROSTATIC CHARGE

BACKGROUND OF THE INVENTION

1. Field of the Invention

The invention relates to a device for protecting an operator when he or she contacts an electrical apparatus arranged in a insulated housing and, more particularly, for protecting electronic devices contained in electrical communication apparatus when the operator carries a high electrostatic charge.

2. Description of the Prior Art

With the use of modern, highly insulating materials, we are increasingly confronted with the problem of electrostatic discharging (ESD). This more or less painful experience is generally known. The electrostatic charge generally arises from the modern equipment of rooms, e.g., synthetic carpeting. Charged individuals suffer an electric shock of greater or lesser intensity when they touch grounded or conductive objects or when they touch objects whose dielectric strength is lower than the charge voltage. Furthermore, when the individuals carrying the high current are discharged, a strong electromagnetic field occurs which, in electrical apparatus, can induce voltages which can themselves lead to malfunctions of the apparatus.

In order to overcome this problem, it is firstly required that the dielectric strength between the contact points be increased. This can be attained, for example, by increasing the distances or interposing insulators. However, this method quickly meets with limitations e.g., in the case of high voltages, redesign of the structure of the electronic equipment is necessary.

The aim of the invention is both to protect the operator from painful discharge currents and also to protect the electronic devices of electrical apparatus from high currents and associated strong electromagnetic fields.

SUMMARY OF THE INVENTION

This aim is fulfilled in accordance with the invention in that in the region of the electrical devices of the apparatus and/or in the danger zone of the components (i.e., a loudspeaker) arranged behind a housing wall, contact paths are provided which have a substantial ohmic resistance (i.e., in the megohm range) and which terminate in the apparatus at a ground point or at a point carrying a low potential.

The equipment of the apparatus with contact paths which have an appreciable resistance allows the operator to discharge gently, so to speak. The equivalent circuit of the contact path can consist of a plurality of series connected resistors, where capacitive resistors leading to ground are arranged between the resistors. If an electrostatically charged individual now touches the contact path, the current which occurs is limited by the resistances and the capacitances.

If, in place of the contact paths with the appreciable resistance, a contact path were provided having a resistance of approximately zero, the equivalent circuit would consist only of a capacitor. In the case of a discharge current, the capacitive resistance of the capacitor would be zero so that no current limitation could be achieved. Due to the high level of the discharge current, which rarely amounts to less than 10A, the electrical apparatus would be endangered by the strength of the magnetic field produced by the high current, so that the operating reliability would be considerably restricted.

In accordance with the invention it is now possible for the contact path to be formed by a resistance path which is arranged on the outer part of the apparatus and which is touched by the operator.

This resistance path can simultaneously represent a graphic character or a decorative strip so that it is non-obtrusive.

In the field of telephone technology, the handset component is particularly vulnerable. Therefore, it is expedient to arrange the resistance path between housing components of a telephone apparatus handset. The resistance path can serve as a decorative strip which is inevitably touched by the operator, thus initiating a gentle discharge of the operator.

The resistance path can advantageously be arranged in an edge zone of the shadow seam, i.e., the seam formed between the housing components, on one of the housing components (e.g., the upper part of the handset housing) and can lead via a pressure contact connection to a point of the other housing component (e.g. The lower part of the handset housing) which is at approximately ground potential. In this way it is only necessary to touch a resistance path on one of the housing components, thereby reducing the manufacturing costs.

In order to achieve a uniformly high resistance, it has proved advantageous that the resistance path should consist of graphite. However, it is also possible for the resistance path to consist of a foil inserted between the housing components. this has the particular advantage that vulnerable apparatus can easily be retrofitted.

To protect operating electrical devices such as push-buttons, displays or loudspeakers it has proved particularly expedient for the contact paths to be applied to a foil which is arranged between an inside surface of the apparatus and the operating electrical devices which are arranged on a carrier and project through to an outer surface of the apparatus or the electrically conductive components (loudspeaker) arranged behind the inside surface.

Virtually no changes are required in the conventional equipment of the electrical apparatus. The apparatus can be retrofitted with the foil as and when needed in order to achieve optimum protection. However, it is not necessary that the contact paths are not directly touched by the operator. At a specific distance and at a specific voltage a corona discharge will, however, occur so that also with this variant the operator is gently discharged.

An improvement in the mode of operation of the foil is achieved if, in the region of the operating electrical devices and/or the loudspeaker, the contact paths are provided with spikes which are punched out of the foil and which, when the apparatus is assembled, are applied to the operating electrical devices and/or the loudspeaker, displays, etc. and terminate at the outer surfaces of the operating electrical devices. As a result, contact inevitably takes place when, for example, a push-button is actuated, again resulting in a gentle discharge.

In the case of individual push-buttons, a foil may be expensive. In this case, the housing wall can be directly provided with a resistance path leading to a ground potential point.

Other features and advantages of the invention will be apparent from the description of the preferred embodiments, and from the claims.

For a fuller understanding of the present invention, reference should now be made to the following detailed description of preferred embodiments of the invention and to the accompanying drawings.

BRIEF DESCRIPTION OF THE DRAWINGS

FIG. 1 is a side view of a telephone station;

FIG. 2 is a view of the interior of an upper housing component of a handset;

FIG. 3 is a partial-section side view of the upper housing component shown in FIG. 2;

FIG. 6 is a section view of a telephone apparatus;

FIGS. 7 and 8 are sectional views through a housing wall illustrating measures in accordance with the invention which provide for a gentle electrostatic discharge;

FIG. 9 is a side view of a transducer arranged in a housing;

FIG. 10 is an equivalent circuit diagram of a telephone station equipped according to the principles of the invention;

DETAILED DESCRIPTION OF THE PREFERRED EMBODIMENTS

Figure 4:
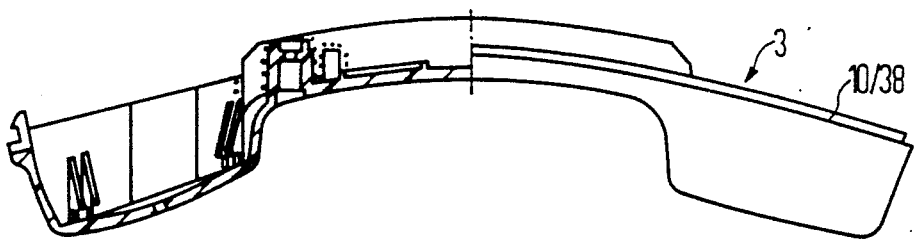
FIG. 4 is a partial-section side view of a lower housing component of a handset.

The telephone station shown in FIG. 1 comprises an apparatus housing 1 on which rests a handset component composed of a housing upper component 2 and a housing lower component 3. A shadow seam which is formed between housing upper component 2 and housing lower component 3 is provided with a resistance path 4. When the handset is gripped by the hands of the operator (shown in phantom) the resistance path is inevitably contacted so that a gentle electrostatic discharge of the operator can take place via the resistance path.

Further details in this respect can be seen from FIGS. 2 and 3 which provide separate diagrams of housing upper component 2 of the handset. A peripheral edge zone 7 which forms shadow seam 4, is coated with a resistive paste composed of graphite and forms a contact path 8. This contact path leads into the interior 9 of housing upper component 2. By means of measures which have not yet been described, contact path 8 is then connected to a point of housing lower component 3 which carries a low potential.

Figure 5:
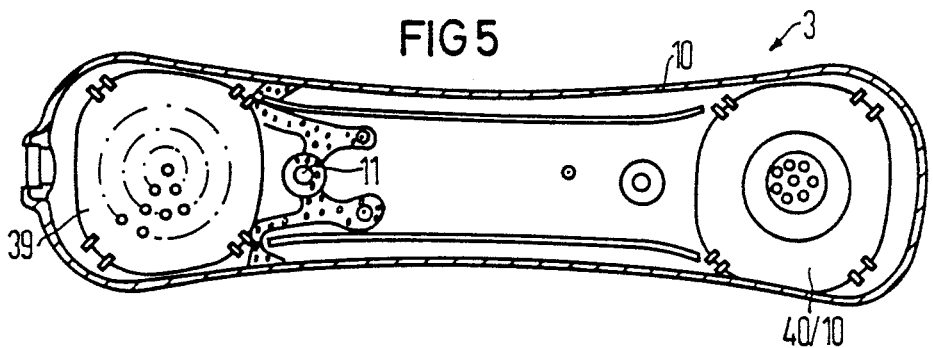
FIG. 5 is a view of the interior of the lower housing component shown in FIG. 4.

Another embodiment is represented in FIGS. 4 and 5 in which two electro-acoustic transducers 9 and 10 are arranged inside housing lower component 3 of a handset. In contrast to the embodiment shown in FIGS. 2 and 3, here housing lower component 3 is provided at its peripheral edge 10 with a highly resistive contact strip 38 which forms the contact path. Strip 38 terminates inside of housing lower component 3 at a contact point 11 which is connected to a point of an electrical circuit which has not yet been described and which carries a low potential.

As previously noted in the background portion of this specification, in addition to components of the handset, operating electronic elements such as push-buttons are also endangered by ESD. If the telephone apparatus is of a design which provides for hands-free conversation, it is unnecessary to lift the handset. However, it is always necessary to actuate a key which initiates the hands-free conversation, as shown in FIG. 6. To allow for a gentle electrostatic discharge of the operator, a key 17 in housing 1 is provided with a contact path by means of which a resistive coating is formed and leads to a point (not shown) carrying a low potential.

Two other possibilities of providing for a gentle electrostatic discharge of an operator are represented in FIGS. 7 and 8. In accordance with FIG. 7, discharge spikes 21, 22 and 23 lead through and terminate in small recesses 18, 19 and 20, respectively, each forming a contact path, and being connected to a point carrying a low potential, e.g. ground. The resistance R which is greater than or equal to 30 megohms, symbolically represents the overall resistance of the contact path.

In accordance with FIG. 8, discharge spikes 21, 22 and 23 are replaced by a discharge cushion 24 which is arranged in a housing 25 and which is connected to ground via additional means.

The attainment of a gentle electrostatic discharge is more problematic in the case of transducers, since the sound apertures therein are to remain unobstructed. As shown in FIG. 9, to prevent or reduce the danger of spark-over, the zone between apparatus housing 26 and housing 27 of the transducer capsules can be provided with a resistive path 28 which leads to ground.

FIG. 10 illustrates the equivalent circuit diagram for a handset equipped in accordance with the invention for so-called gentle electrostatic discharge. The resistive path can be represented by a series of resistors R between which capacitors C are connected to ground potential. In the case of a gentle electrostatic discharge, the currents flow to ground via both the resistors and the capacitors, thus avoiding a high peak current. If a finger 42 of a human operator—represented by the resistance RM of 150 ohms and the capacitance CM of 150 pF—carries a high potential level that touches the edge zone of the handset, the plurality of resistors and capacitors provide for a gentle electrostatic discharge. In the equivalent circuit diagram it can also be seen that ground line 29 leads to a microphone 30 and to a ground point 31 of the apparatus housing.

Figure 11:
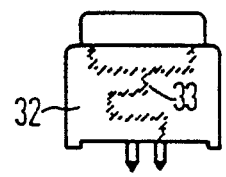
FIG. 11 is a side view of a push-button.

The embodiment shown in FIG. 11 can be used to protect push-buttons, luminescent diodes or displays from spark-over and to facilitate a gentle electrostatic discharge. In accordance with this embodiment, the housing exterior 32 is provided with a resistive path 33 which leads to a ground potential point.

Figure 12:
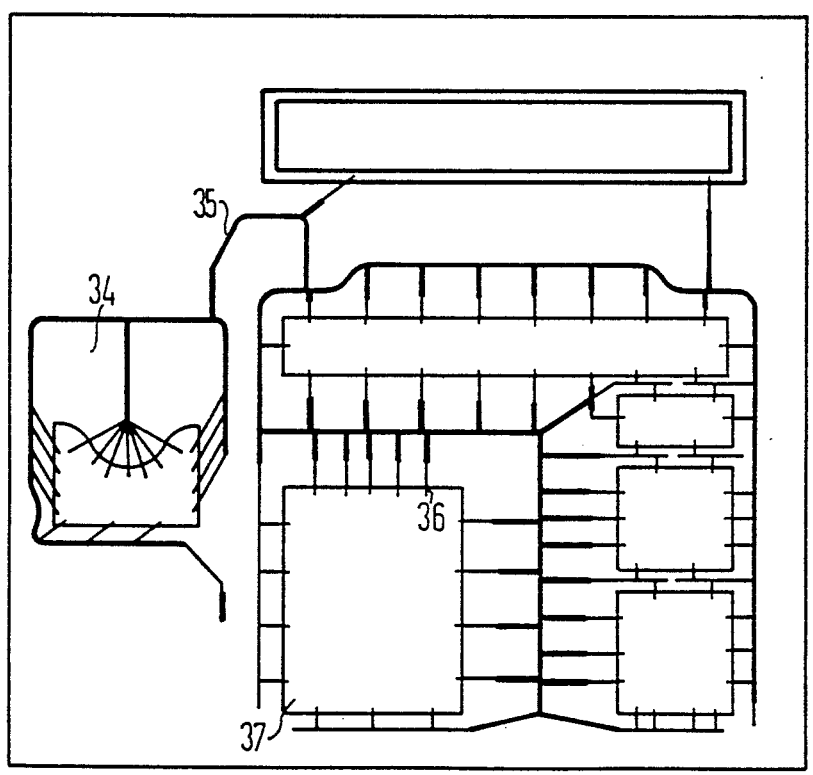
FIG. 12 is a diagram of a foil provided with resistance paths.

FIG. 12 shows another possibility of protecting such components. FIG. 12 shows resistive paths 35 which are applied to a foil 34 by screen printing and which are connected by punched-out spikes 36. Spikes 36 are arranged, for example, on a push-button dialing block, whose later location is indicated by the free zone 37. If this foil is now positioned between the housing of a telephone and the housing of a push-button dialing block, the punched-out spikes closely contact the housing of the push-button dialing block and when they are of the correct formation can extend to the outer edge of the telephone housing, so that on contact with the operator a gentle discharge is achieved.

Thus, there has been shown and described novel apparatus for gently discharging electrostatic charges when an operator touches an electrical equipment which fulfills all the objects and advantages sought therefore. Many changes, modifications, variations and other uses and applications of the subject invention will, however, become apparent to those skilled in the art after considering this specification and the accompanying drawings which disclose a preferred embodiments thereof. All such changes. modifications, variations and other uses and applications which do not depart from the spirit and scope of the invention are deemed to be covered by the invention which is limited only by the claims which follow.

We claim:

1. Apparatus for protecting an operator who contacts a telephone apparatus handset arranged in an insulated housing including at least first and second housing components and for protecting electronic devices which comprise the telephone apparatus, in the event the operator carries a high electrostatic charge, comprising:
    at least one resistive contact path having a relatively appreciable ohmic resistance (e.g., in the megohm range) and arranged proximate an outer part of said insulating housing which is touched by the operator, wherein a first end of said resistive contact path is arranged between said housing components and located in the region of said electronic devices and a second end of said resistive contact path terminates at a low potential point of the handset.

2. Apparatus according to claim 1, wherein said resistive contact path consists of graphite.

3. Apparatus according to claim 1, wherein said resistive contact path consists of a foil inserted between said housing components.

4. Apparatus for protecting an operator who contacts of a telephone apparatus handset arranged in an insulated housing including at least first and second housing components and for protecting electronic devices which comprise the telephone apparatus, in the event the operator carries a high electrostatic charge, comprising:
    at least one resistive contact path having a relatively appreciable ohmic resistance (e.g., in the megohm range) and arranged proximate an outer part of said insulating housing which is touched by the operator, wherein said resistive contact path is arranged on one of said housing components in the region of a shadow seam formed between said housing components, and has a first end which is located in the region of said electronic devices and a second end which leads via a pressure-contact connection to a point of the other one of said housing components which includes a low potential point.

5. Apparatus according to claim 4, wherein said resistive contact path consists of graphite.

6. Apparatus according to claim 4, wherein said resistive contact path consists of a foil inserted between said housing components.

* * * * *